(12) United States Patent
Musacchio et al.

(10) Patent No.: US 10,465,808 B2
(45) Date of Patent: Nov. 5, 2019

(54) SPRING-ENERGIZED CHECK VALVE

(71) Applicant: Waters Technologies Corporation, Milford, MA (US)

(72) Inventors: Jeffrey Musacchio, Sharon, MA (US); Joseph D. Michienzi, Plainville, MA (US); Keith Fadgen, Hope Valley, RI (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 0 days.

(21) Appl. No.: 16/323,637

(22) PCT Filed: Aug. 7, 2017

(86) PCT No.: PCT/US2017/045687
§ 371 (c)(1),
(2) Date: Feb. 6, 2019

(87) PCT Pub. No.: WO2018/031443
PCT Pub. Date: Feb. 15, 2018

(65) Prior Publication Data
US 2019/0186485 A1    Jun. 20, 2019

Related U.S. Application Data

(60) Provisional application No. 62/371,963, filed on Aug. 8, 2016.

(51) Int. Cl.
*F16K 15/14*     (2006.01)
*F04B 53/10*     (2006.01)
(Continued)

(52) U.S. Cl.
CPC ............ *F16K 15/142* (2013.01); *F04B 53/10* (2013.01); *F16K 15/147* (2013.01);
(Continued)

(58) Field of Classification Search
CPC .... F16K 15/142; F16K 15/147; F16K 15/148; F16J 15/3212
(Continued)

(56) References Cited

U.S. PATENT DOCUMENTS 1,636,888 A    7/1927  Wishart
2,264,062 A *  11/1941 Wilder ................ F16J 15/3212
                                                          277/569
(Continued)

OTHER PUBLICATIONS

International Preliminary Report on Patentability in PCT/US2017/045687 dated Feb. 21, 2019; 6 pages.
(Continued)

*Primary Examiner* — Umashankar Venkatesan
(74) *Attorney, Agent, or Firm* — Schmeiser, Olsen & Watts LLP; William G. Guerin (57) ABSTRACT

A check valve includes a first valve body having a chamber in which second and third valve bodies are located. The check valve also includes a spring-energized seal disposed in the chamber. The spring-energized seal includes a compliant seal body having an annular shape and a resilient member, such as a cantered spring or O-ring, disposed in a pocket of the seal body. The resilient member applies a force to portions of the seal body to prevent the passage of fluid from a valve inlet port to a valve outlet port unless the differential fluid exceeds the cracking pressure of the check valve.

16 Claims, 8 Drawing Sheets

(51) Int. Cl.
*G01N 30/02* (2006.01)
*G01N 30/20* (2006.01)
*F16J 15/3212* (2016.01)

(52) U.S. Cl.
CPC .......... *F16K 15/148* (2013.01); *G01N 30/02* (2013.01); *G01N 30/20* (2013.01); *F16J 15/3212* (2013.01)

(58) Field of Classification Search
USPC .................. 137/852, 857; 251/175, 176, 186
See application file for complete search history.

(56) References Cited

U.S. PATENT DOCUMENTS

| | | | |
|---|---|---|---|
| 3,810,716 A | 5/1974 | Abrahams et al. | |
| 4,245,963 A | 1/1981 | Hutchins et al. | |
| 5,078,412 A * | 1/1992 | Baumgarth | F02K 1/805 239/127.1 |
| 6,968,858 B2 | 11/2005 | Kuehn et al. | |
| 7,640,841 B2 * | 1/2010 | An | F16J 15/3212 277/553 |
| 8,544,850 B2 * | 10/2013 | Balsells | F16J 15/166 277/511 |
| 8,671,975 B2 | 3/2014 | Charlton et al. | |
| 9,488,277 B2 * | 11/2016 | Shreve | F04B 1/0448 |
| 2006/0159571 A1 * | 7/2006 | Hinz | B60T 8/4031 417/440 |
| 2010/0166582 A1 * | 7/2010 | Racicot | F04B 39/041 417/437 |
| 2010/0251896 A1 | 10/2010 | Kellogg | |
| 2015/0129057 A1 | 5/2015 | Shreve et al. | |
| 2017/0172018 A1 * | 6/2017 | Dilmaghanian | H05K 9/0016 |

OTHER PUBLICATIONS

International Search Report & Written Opinion in PCT/US2017/045687 dated Oct. 31, 2017; 7 pages.

* cited by examiner

SPRING-ENERGIZED CHECK VALVE

RELATED APPLICATION

This application claims the benefit of the earlier filing date of U.S. Provisional Patent Application No. 62/371,963, filed Aug. 8, 2016 and titled "Spring-Energized Check Valve," the entirety of which is incorporated herein by reference.

FIELD OF THE INVENTION

The invention relates generally to fluid control valves. More particularly, the invention relates to a spring-energized check valve having a low cracking pressure.

BACKGROUND

Instruments used in analytical and preparative chemistry often include valves to control the flow of fluids. Check valves are one important class of flow-control valves and are typically utilized to permit fluid flow in one direction while impeding fluid flow in the reverse direction. Liquid chromatography systems, for example, typically include check valves in fluid communication with respective inlet and outlet ports of a displacement pump to control the direction of fluid flow through the pump.

For example, U.S. Pat. No. 3,810,716 to Abrahams et al. describes inlet and outlet check valves applied to a high-pressure chromatography reciprocating two-piston pump. The pump employs an inlet and an outlet check valve respectively on each of two displacement chambers or cylinders. The pump has a parallel configuration which delivers fluid to a downstream receiving system alternately from two pump cylinders; each cylinder is in direct fluid communication with the receiving system during a portion of the pump cycle. The alternating pattern of fluid delivery allows one pump cylinder to be refilled while delivery from the other pump cylinder sustains the desired pump output flow rate to the downstream system.

The inlet and outlet check valves associated with each cylinder in this parallel configuration allow each cylinder to communicate either with an inlet fluid pathway from a solvent reservoir or with an outlet fluid pathway to the downstream receiving system. The operation and location of the check valves substantially prevents the backflow of fluid from the pressurized system into a pump cylinder that is undergoing refill at substantially atmospheric pressure.

Another common configuration of a high-pressure pump for liquid chromatography is a serial configuration described, for example, in U.S. Pat. No. 4,245,963 to Hutchins et al. Liquid inspired at a pump intake is directed serially through a first pump cylinder and a second pump cylinder. Only a single inlet and a single outlet check valve are utilized. The coordinated motion of respective first and second pistons interacts cooperatively with the actions of the inlet and the outlet check valves to achieve a substantially constant output flow rate of liquid to a downstream receiving system.

As with the parallel pump configuration, a single drive motor may be used to affect the coordinated motion of the two pistons using appropriate gearing or equivalent drive elements. Alternatively, a separate motor may be allocated for the drive of each piston, which can allow greater operational flexibility in motion coordination.

A ball-and-seat type of chromatography pump check valve is particularly common. A typical configuration employs a stationary seat and a ball that is capable of being displaced toward or away from the seat. In a passive ball-and-seat check valve, fluid flow in one direction urges the ball against the seat, blocking the flow of fluid. Fluid flow in the opposite direction urges the ball away from the seat, opening a pathway through the valve. Some passive check valves include a spring that holds the ball against the seat until a differential fluid pressure across the valve exceeds a threshold pressure determined by the force applied by the spring. This differential pressure is often referred to as the "cracking pressure." A low cracking pressure allows for improved pump performance because any pressure differential results in a flow disturbance when the check valve is open. Generally, the flow disturbance is more pronounced with greater cracking pressure.

The ball for a chromatography pump check valve is commonly fabricated from ruby while the seat is commonly fabricated from sapphire (both ruby and sapphire are forms of crystalline aluminum oxide.) Alternatively, check valve balls and seats are fabricated from, for example, aluminum-oxide based ceramics. These materials are chosen for desired properties, for example, for their chemical inertness, resistance to wear, machinability, and/or stiffness.

Chromatography pumps are generally high-precision devices, designed to produce substantially stable and reproducible solvent flows at delivery pressures of as much as thousands of pounds per square inch (psi) or greater (i.e., tens of megaPascals (MPa) or greater). Back-leakage of a check valve can degrade or destroy the desired relationship between a control input (such as a pump step-motor step rate or step count) and a volume delivery output of chromatography solvent. Therefore, considerable effort has been expended by ball-and-seat check valve manufacturers to produce balls that are highly spherical and that have an excellent surface finish. A corresponding effort has been expended by manufacturers to produce seats having a spherical or conical sealing surface with a close tolerance as well as an excellent surface finish.

Though providing a good seal when new, many conventional valves become fouled in service by foreign matter that lodges on either the ball or the seat sealing surface. The fouling at times is transient, where the fouling substance is swept downstream on a subsequent valve actuation or more permanent, where restoration of proper valve function may require valve disassembly and aggressive cleaning or component replacement.

While fouling matter resides on the ball or seat, the check valve may be rendered partially or wholly inoperable due to a failure to properly seal against reverse flow. In another failure mode, the ruby and sapphire materials may become stuck together in the presence of particular solvents, rendering the valve inoperable because it cannot enable fluid flow in the forward direction.

U.S. Pat. No. 8,671,975 to Charlton et al. describes a check valve that uses a compliant member on a moveable member in which a coil is used to apply a force to urge the moveable member toward a valve seat. Pressure may further assist in maintaining a seal when the valve is in a closed state. The cracking pressure that is achievable in the disclosed valve may have a cracking pressure high enough to introduce pressure disturbances that are unacceptable in some instance.

Typical check valves require axial flow of the fluid through the device and therefore cannot accommodate configurations in which the direction of flow changes, for example, when inlet and outlet flow paths are not coaxial. Some ball and seat check valves are required to be oriented vertically such that gravity locates the ball in the seat under conditions without fluid flow. Moreover, such valves are susceptible to debris which may be disposed between the ball and the seat and which prevents proper seating necessary for sealing.

SUMMARY

In one aspect, the invention features a check valve that includes a first valve body, a second valve body, a third valve body and a first spring-energized seal. The first valve body has a cylindrical chamber defined by a chamber wall comprising a cylindrical surface and an end surface, a first channel extending from a first external surface to a first port at the end surface of the chamber wall and a second channel extending from a second external surface to a second port at the cylindrical surface of the chamber wall. The second valve body is disposed in the chamber and has a cylindrical external surface and a flange at one end. The third valve body has a cylindrical surface and is disposed in the chamber between the flange and the end surface of the chamber wall at the inlet port. The first spring-energized seal is disposed in the chamber and includes a first compliant seal body and a resilient member. The first compliant seal body has an annular shape, a seal circumferential surface and a pocket. The seal circumferential surface is in contact with the cylindrical surface of the chamber wall or the cylindrical surface of the third valve body. The resilient member is disposed in the pocket of the first compliant seal body. The resilient member is configured to apply a force to urge a first portion of the first compliant seal body against a region of the end surface of the chamber wall surrounding the inlet port and to urge a second portion of the first compliant seal body against the flange of the second valve body.

In some embodiments, the second valve body and the third valve body are formed as a single integral body. In one embodiment, the check valve further includes a second spring-energized seal disposed in the chamber and having a second compliant seal body having a pocket with a spring disposed therein. The second compliant seal body is configured to apply a force to urge a first portion of the second compliant seal body against the cylindrical surface of the chamber wall and to urge a second portion of the second compliant seal body against the cylindrical external surface of the second valve body. In a further embodiment, the first and second spring-energized seals are formed as a single integral seal assembly.

In another aspect, the invention features a check valve that includes a first valve body, a second valve body, a third valve body and a first spring-energized seal. The first valve body has a cylindrical chamber defined by a chamber wall comprising a cylindrical surface and an end surface, a first channel extending from a first external surface to a first port at the end surface of the chamber wall and a second channel extending from a second external surface to a second port at the cylindrical surface of the chamber wall. The second valve body is disposed in the chamber and has a cylindrical external surface and a flange at one end. The third valve body has a cylindrical surface and is disposed in the chamber between the flange and the end surface of the chamber wall at the inlet port. The first spring-energized seal is disposed in the chamber and includes a first compliant seal body and a resilient member. The first compliant seal body has an annular shape, a seal circumferential surface and a pocket. The seal circumferential surface is in contact with the end surface of the chamber wall or the flange of the second valve body. The resilient member is disposed in the pocket of the first compliant seal body. The resilient member is configured to apply a force to urge a first portion of the first compliant seal body against the cylindrical surface of the chamber wall and to urge a second portion of the first compliant seal body against the cylindrical surface of the third valve body.

In some embodiments, the check valve further includes a backup ring disposed between the seal circumferential surface of the first compliant seal body and the flange of the second valve body. In some embodiments, the second valve body and the third valve body are formed as a single integral body. In one embodiment, the check valve further includes a second spring-energized seal disposed in the chamber and having a second compliant seal body having a pocket with a spring disposed therein. The second compliant seal body is configured to apply a force to urge a first portion of the second compliant seal body against the cylindrical surface of the chamber wall and to urge a second portion of the second compliant seal body against the cylindrical external surface of the second valve body. In a further embodiment, the first and second spring-energized seals are formed as a single integral seal assembly.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure.

In various types of liquid chromatography systems, pumping systems are used to provide a pressurized fluid. One type of piston pump system used to deliver a high pressure fluid includes a primary pump and an accumulator pump. A check valve is disposed between the outlet of the primary pump and the inlet of the accumulator pump to allow a forward fluid flow and to prevent a backward flow of fluid into the chamber of the primary pump.

During operation, the primary pump receives a liquid, such as a chromatography solvent (or mixture of solvents) from a solvent source. During an accumulator piston delivery stroke, liquid is provided at the accumulator outlet at a desired flow rate and the check valve is in a closed state that prevents liquid from flowing back to the primary pump. When the accumulator piston executes an intake stroke, the piston of the primary pump executes a delivery stroke that causes liquid to flow through the check valve and into the accumulator chamber to refill the accumulator chamber and to simultaneously provide flow from the outlet of the accumulator pump. The flow rate of the liquid delivered by the primary pump during a delivery stroke is greater than the flow rate of the liquid delivered by the accumulator pump during a delivery stroke. Consequently, the accumulator chamber can be refilled while maintaining a constant flow rate at the outlet of the accumulator pump throughout the duration of each pumping system cycle.

The above described configuration is one example of the use of a check valve in which a low cracking pressure is desirable. A reduction in the flow disturbances occurring upon the opening of the check valve can reduce errors in chromatographic separations in which accurate contributions of solvents are required.

In various embodiments described below, a check valve includes a first valve body having a chamber in which a second valve body and a third valve body are located. The third valve body is structured to include a surface configured to engage a wall of the chamber at a region where an inlet allows fluid to flow into the chamber. The check valve also includes a spring-energized seal located in the chamber. The spring-energized seal includes a compliant seal body having an annular shape and a resilient member, such as a cantered spring or O-ring, disposed in a pocket of the seal body. The resilient member applies a force to portions of the seal body to prevent the passage of fluid further into the chamber unless the fluid pressure exceeds the cracking pressure of the check valve. Advantageously, in comparison with conventional ball and seat check valves, the spring-energized check valve is less affected by debris and does not require a particular orientation with respect to gravity.

Figure 1:
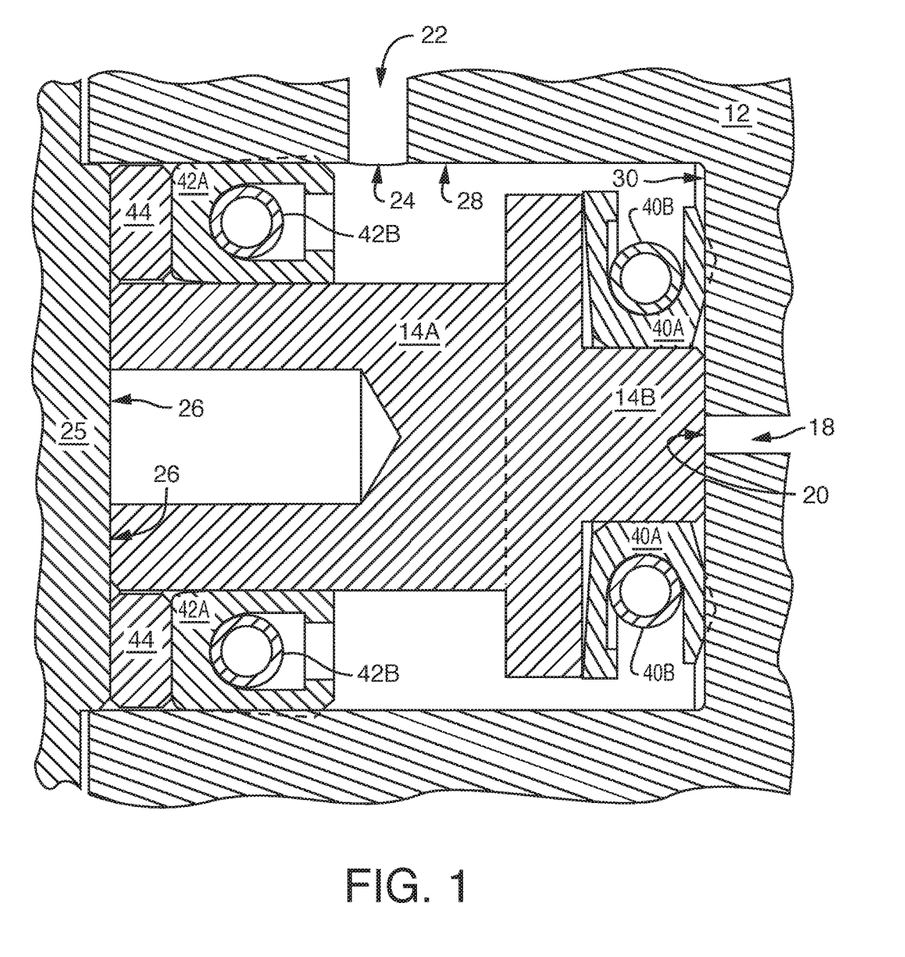
FIG. 1 is a cross-sectional view of a portion of an embodiment of a check valve that can be used in a liquid chromatography system.

FIG. 1 is a cross-sectional view of a portion of an embodiment of a check valve that may be used, for example, in a liquid chromatography system. The check valve includes a first valve body 12 a second valve body 14A and a third valve body 14B that is adjacent to the second valve body along the dashed vertical line. As illustrated, the second and third valve bodies 14A and 14B (generally 14) are formed as a single integral body although in other embodiments the second and third valve bodies 14A and 14B may be discrete bodies. Only a portion of the first valve body 12 is shown in the figure. The valve bodies 12 and 14 may be made from a metal such as titanium or stainless steel. Alternatively, for some applications the second and/or third valve bodies 14 can be made of a plastic. The first valve body 12 includes a chamber defined by a chamber wall. The first valve body 12 also includes an inlet channel 18 that extends from a first external surface (not shown) through the first valve body 12 to an inlet port 20 at the chamber wall and an outlet channel 22 that extends from the first external surface or a second external surface (not shown) and passes through the first valve body 12 to an outlet port 24 in the chamber wall. The chamber has a nominally cylindrical shape with a cylindrical surface 28 and extends at the right from an end surface 30 of the chamber wall that includes the inlet port 20. An end plate 25 with a surface 26 is located at the left side of the chamber. The end plate 25 may be secured to the first valve body 12 using bolts or screws (not shown) to fully enclose the chamber. When the check valve operates in an open state, liquid flows through the inlet channel 18 and into the chamber, and exits the chamber through the outlet channel 22. The check valve operates in a closed state when the pressure at the outlet port 24 is greater than the pressure at the inlet port 20. Under this condition, liquid would flow in the reverse direction, i.e., liquid would flow from the outlet channel 22 into the chamber and then exit through the inlet channel 18; however, a spring-energized seal 40 described below prevents flow in this reverse direction. As used herein, a spring-energized seal is a seal that includes a resilient member, such as a spring or O-ring, to apply a spring-like force to one or more portions of a compliant seal body.

Figure 2:
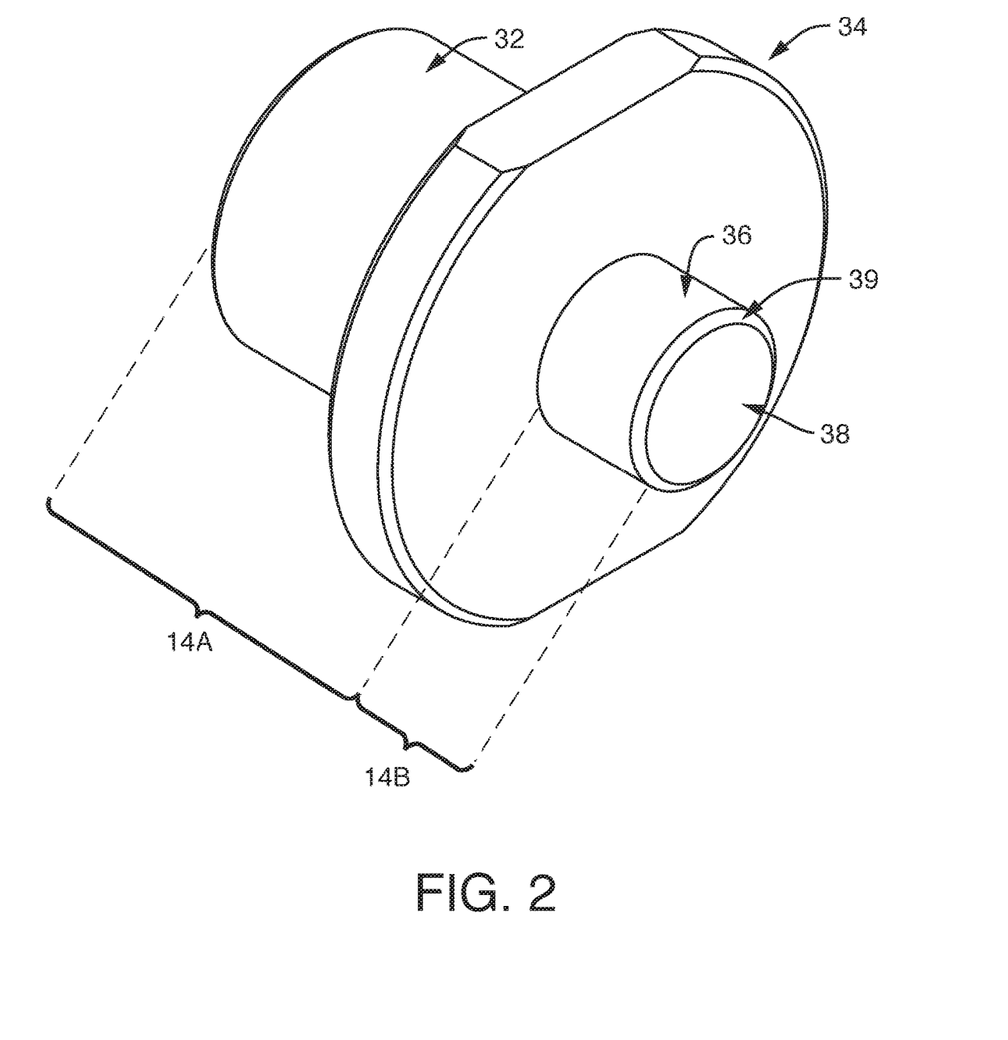
FIG. 2 is a perspective view of a single integral body comprising the second and third valve bodies of FIG. 1.

Reference is also made to the perspective view of FIG. 2 showing second and third valve bodies 14A and 14B, respectively, as a single integral body. The second valve body 14A has a cylindrical surface 32 and a flange 34. The third valve body 14B includes a cylindrical surface 36 between the flange 34 and a wall engagement surface 38, and is adapted to receive the spring-energized seal 40 as described below. There is a small chamfered surface 39 that "transitions" from the circumferential surface 34 to the wall engagement surface 38.

The wall engagement surface 38 may include one or more channels to permit the flow of liquid if the surface 38 is in contact with the end surface 30 of the chamber wall. Alternatively, the wall engagement surface 38 may be displaced from the end surface 30 by a small distance to permit liquid flow. By way of a non-limiting example, the displacement may be approximately 0.001 in. (25 µm). In another alternative configuration, the third valve body 14B may be a fit or other porous body. In this configuration, the porous structure of the frit permits liquid to flow into the chamber when the wall engagement surface 38 is in contact with the end surface 30 of the chamber wall. Advantageously, the porous object can filter out particulate matter, for example, particles shed from a plunger seal of an upstream pump. Although some liquid pathways through the porous object may clog with the particulate matter over time, other pathways remain available so that the liquid flow remains substantially uninterrupted.

Figure 3:
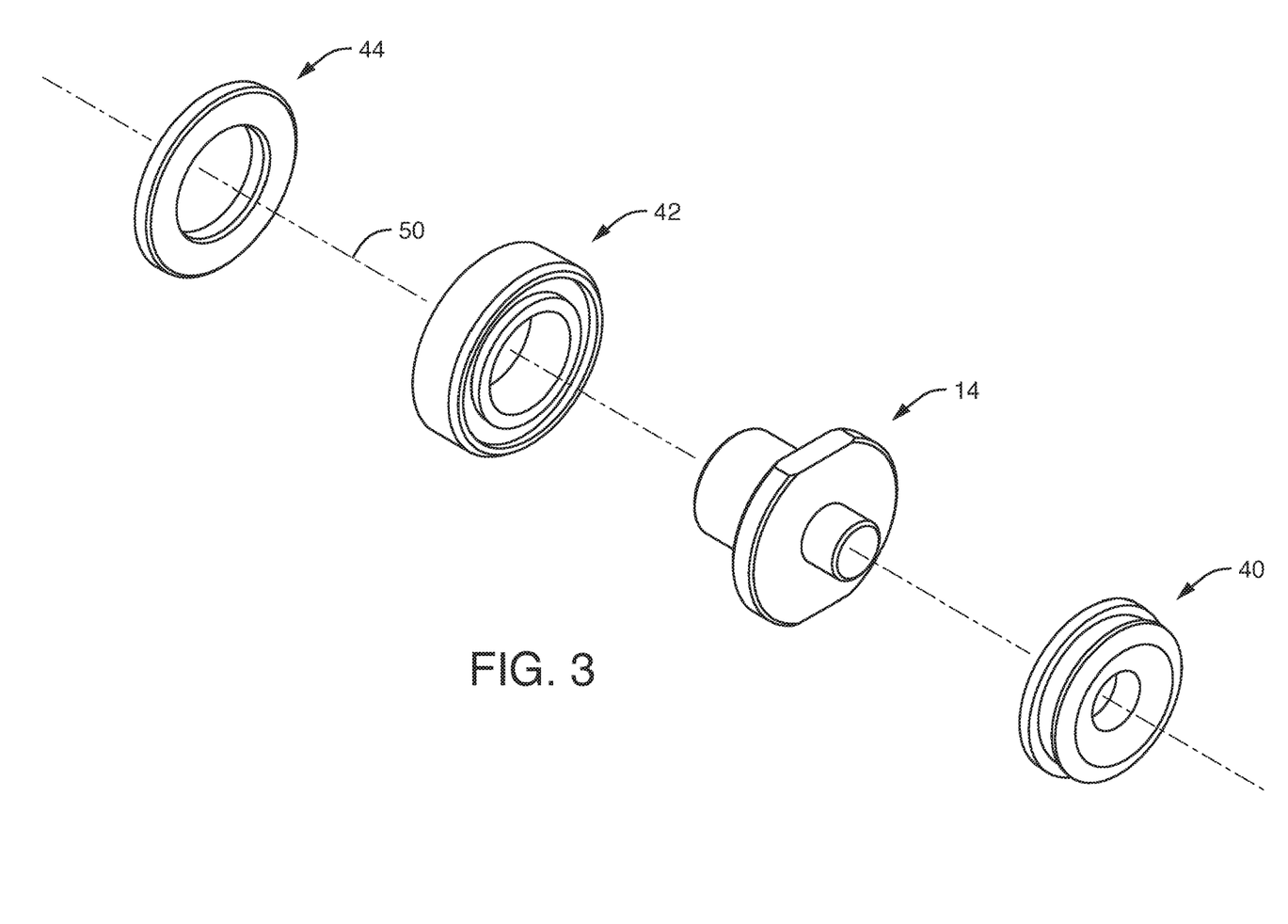
FIG. 3 is an exploded view of certain components located inside the chamber of the check valve of FIG. 1.

The check valve further includes a first spring-energized seal 40, a second spring-energized seal 42 and a backup ring 44. In one example, the backup ring 44 is made from polyether ether ketone (PEEK). The second spring-energized seal 42 and backup ring 44 are used to seal the chamber at the left side in FIG. 1. Reference is also made to FIG. 3 which, for clarity, shows an exploded view of certain components located inside the chamber along an axis 50 which is co-linear with the inlet channel 18.

Figure 4A:
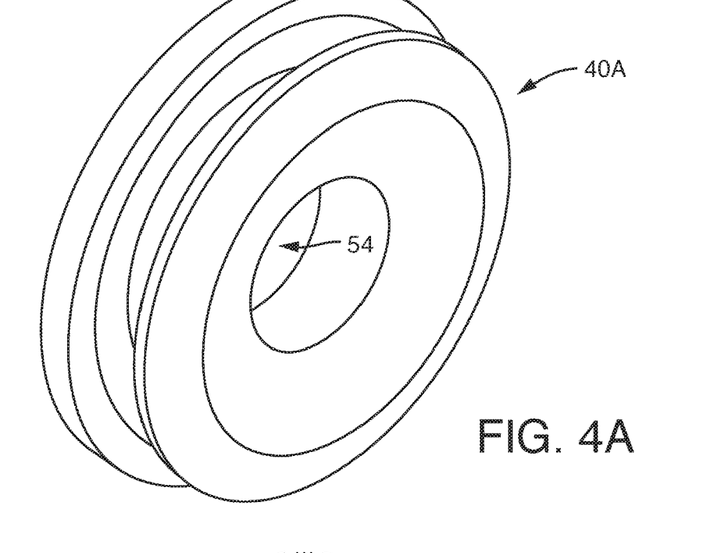
FIG. 4A and FIG. 4B show a perspective view and a cross-sectional view, respectively, of the compliant seal body of the first spring-energized seal in FIG. 1.

The first spring-energized seal 40 includes a compliant seal body 40A and a resilient member such as a coil spring 40B having a closed circular path. In other embodiments, an O-ring or other type of resilient member is used in place of the spring. The seal body 40A is shown in more detail without the spring 40B in the perspective view of FIG. 4A and in a cross-sectional view with the spring 40B in FIG. 4B. The seal body 40A is formed from a compliant material such as polytetrafluoroethylene (PTFE) (e.g., DURON®) and has an annular shape, a pocket 52 which holds the spring 40B, and a central opening 54. The central opening 54 is defined by a seal circumferential surface 56 and has a diameter that is sufficient to pass the third valve body 14B such that the seal circumferential surface 56 is in contact with the cylindrical surface 36 of the third valve body 14B. The seal body 40A includes a first portion (lip) 58 that is adjacent to a region of the chamber wall 16 that surrounds the inlet port 20 and a second portion (lip) 60 that is adjacent to the flange 34 of the second valve body 14A. The first and second portions 58 and 60 and the intervening base of the seal body 40A substantially surround the pocket 52 and retain the spring 40B in place. In some embodiments, the spring 40B may be a cantered metal spring such as a helical spring or spiral pitch spring.

Figure 4B:
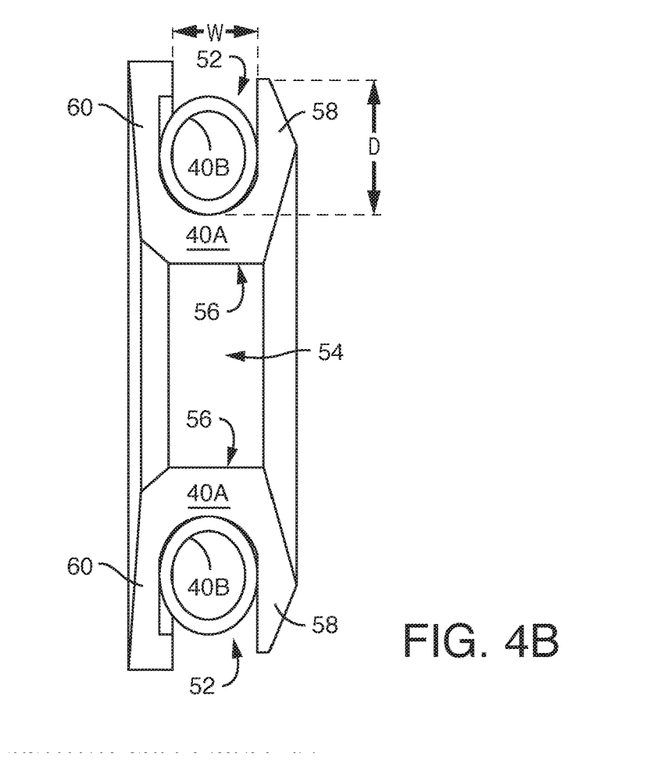

The first spring-energized seal 40 is under compression such that the resilient member, i.e., spring 40B, applies a force to urge the first portion 58 of the seal body 40A against the end surface 30 of the chamber wall surrounding the inlet port 20 and to urge the second portion 60 of the seal body 40A against the flange 34 of the second valve body 14.

By way of a non-limiting example, the width W and depth D of the pocket 52 may be less than 0.05 in. (1.3 mm) and the diameter of the central opening 54 may be approximately 0.09 in. (2.3 mm).

The second spring-energized seal 42 may be constructed similar to seals used with reciprocating plunger pumps. The second spring-energized seal 42 may have a seal body 42A formed of a similar compliant material to that of the seal body 40A and a cantered metal spring 42B similar to the seal spring 40B although the dimensions and applied spring forces may differ. The backup ring 44 prevents a seal made of a compliant material having a low yield strength from extruding past the ring 44 toward the endplate 25. Unlike the first spring-energized seal 40, the second spring-energized seal 42 is intended to prevent the flow of liquid past the seal 42 at all times.

Referring again to FIG. 1, the check valve is configured to pass a liquid flowing through the inlet channel 18 and the inlet port 20 through the chamber and out through the outlet port 24 and outlet channel 22. The weak force applied by the spring 40B in the first spring-energized seal 40 is not sufficient to prevent the flow of liquid past the first and second portions 58 and 60 of the seal body 40A as long as the fluid pressure is at least as great as the cracking pressure. In some embodiments, the cracking pressure may be as low as 10 psi (0.07 MPa) or less.

When the pressure at the outlet port 24 increases to be greater than the pressure at the inlet port 20, the flow of liquid begins to reverse direction; however, the configuration of the first spring-energized seal 40 prevents liquid from exiting through the inlet channel 18. More specifically, the increased fluid pressure inside the chamber applies further force to urge the first and second portions 58 and 60 of the seal body 40A against the end surface 30 of the chamber wall and the flange 34.

The cracking pressure for a particular application can be achieved by proper selection of the first spring-energized seal 40 and/or the degree of compression of the seal 40 inside the chamber. For a seal body geometry that is fixed, the selection of a spring that applies an appropriate force enables the seal 40 to achieve the desired cracking pressure. Spring selection may be based on a variety of spring properties such as the wire diameter, coil size, the number of coils and spring material.

Figure 5:
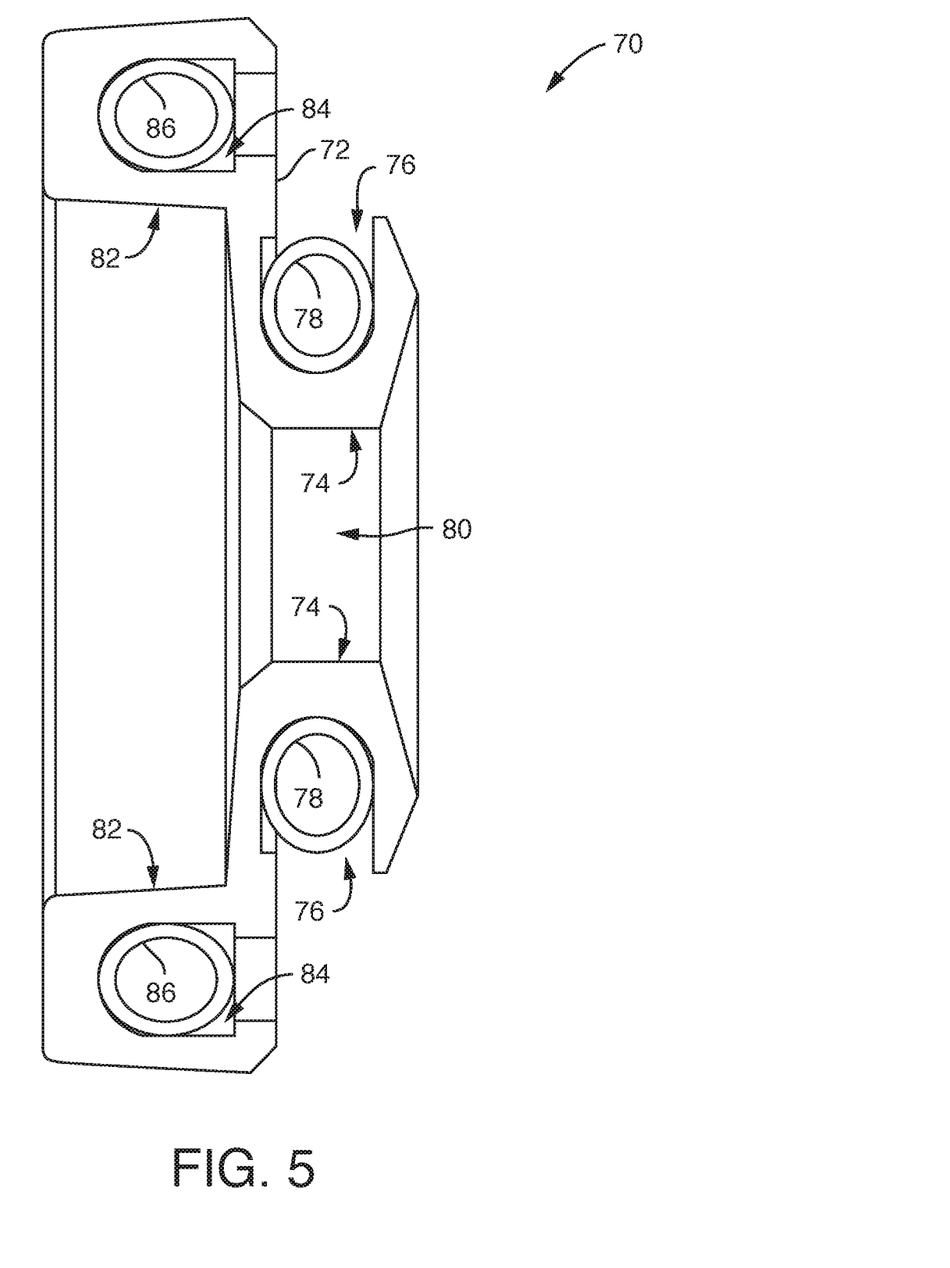
FIG. 5 is a cross-sectional illustration of an integral seal assembly used in an alternative embodiment of a spring-energized check valve.

FIG. 5 is a cross-sectional illustration of an integral seal assembly 70 that may be used in an alternative embodiment of a spring-energized check valve. The seal assembly 70 is used in place of the two spring-energized seals 40 and 42 of FIG. 1 with the second and third valve bodies modified to have similar diameters.

The seal assembly 70 includes a seal body 72 formed from a compliant material such as PTFE. The compliant seal body 72 has an axial seal portion on the right side of the figure and a radial seal portion on the left side of the figure. The axial seal portion has an inner circumferential surface 74 and a pocket 76 that holds a spring 78. The inner circumferential surface 74 surrounds a central opening 80. When installed on the second and third valve bodies 14 (see FIGS. 1 and 2), the third valve body 14B extends through the opening 80 so that the inner circumferential surface 74 abuts the cylindrical surface 36. The radial seal portion also has an inner circumferential surface 82 and a pocket 84 that holds a second spring 86. The axial and radial seal portions are coupled together at the ends of adjacent portions, or lips, as illustrated. The spring 78 in the pocket 76 applies a force to urge a portion of the axial seal portion against the end surface of the chamber wall that surrounds the inlet port 20 and urges a second portion of the axial seal portion against the flange 34 of the second valve body 14A. The spring 86 in the pocket 84 applies a force to urge a portion of the radial seal portion against the cylindrical surface 28 of the chamber wall and urges another portion of the radial seal portion against the cylindrical surface 32 of the second valve body 14A. The seal assembly 70 functions to restrict and permit the flow of liquid in an analogous manner to the operation of the separated spring-energized seals 40 and 42 of FIG. 1.

Figure 6:
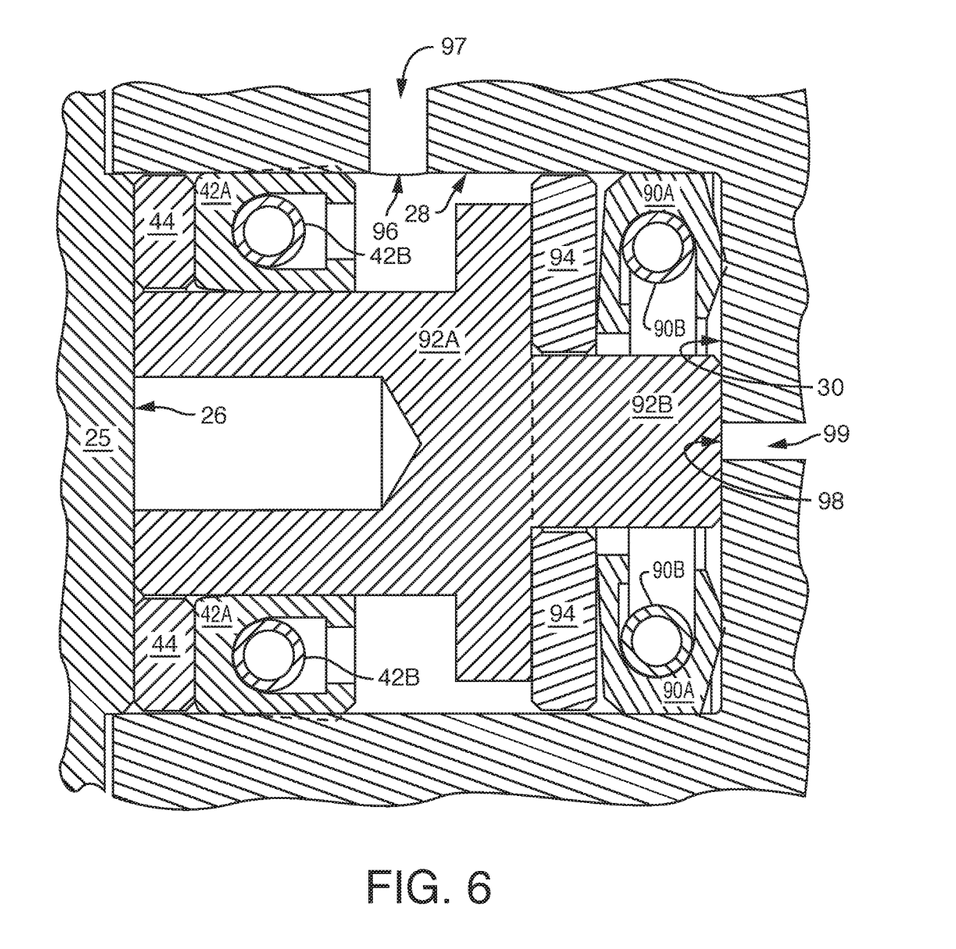
FIG. 6 is a cross-sectional view of a portion of another embodiment of a check valve.

In the embodiments shown in FIG. 1 and described above, the first spring-energized seal is arranged so that its circumferential surface is in contact with the cylindrical surface 36 of the third valve body 14B; however, it will be recognized that other configurations according to the principles described herein are suitable for various applications. For example, a first spring-energized seal may be configured so that the seal circumferential surface has a greater diameter than the pocket and resilient member (spring 90B) as shown in FIG. 6. More specifically, the seal circumferential surface is in contact with the cylindrical surface 28 of the chamber wall. The spring 90B urges the first and second portions of the first compliant seal body 90 against the end surface 30 of the chamber wall and the flange of the second valve body 92A. The dimensions of the second and third valve bodies 92A and 92B are different from their counterpart bodies 14A and 14B in FIG. 1 to accommodate the differences in the first spring-energized seals and to further accommodate a backup ring 94 used to prevent the first complaint seal body 90A from extruding to the left into the chamber. In the illustrated embodiment, the flow of liquid is reversed, that is, liquid flows in through inlet channel 97 into the chamber through an inlet port 96 in the cylindrical surface 28 of the chamber wall. Liquid exits the chamber through an outlet port 98 in the end surface 30 of the chamber wall and flows through an outlet channel 99.

Figure 7:
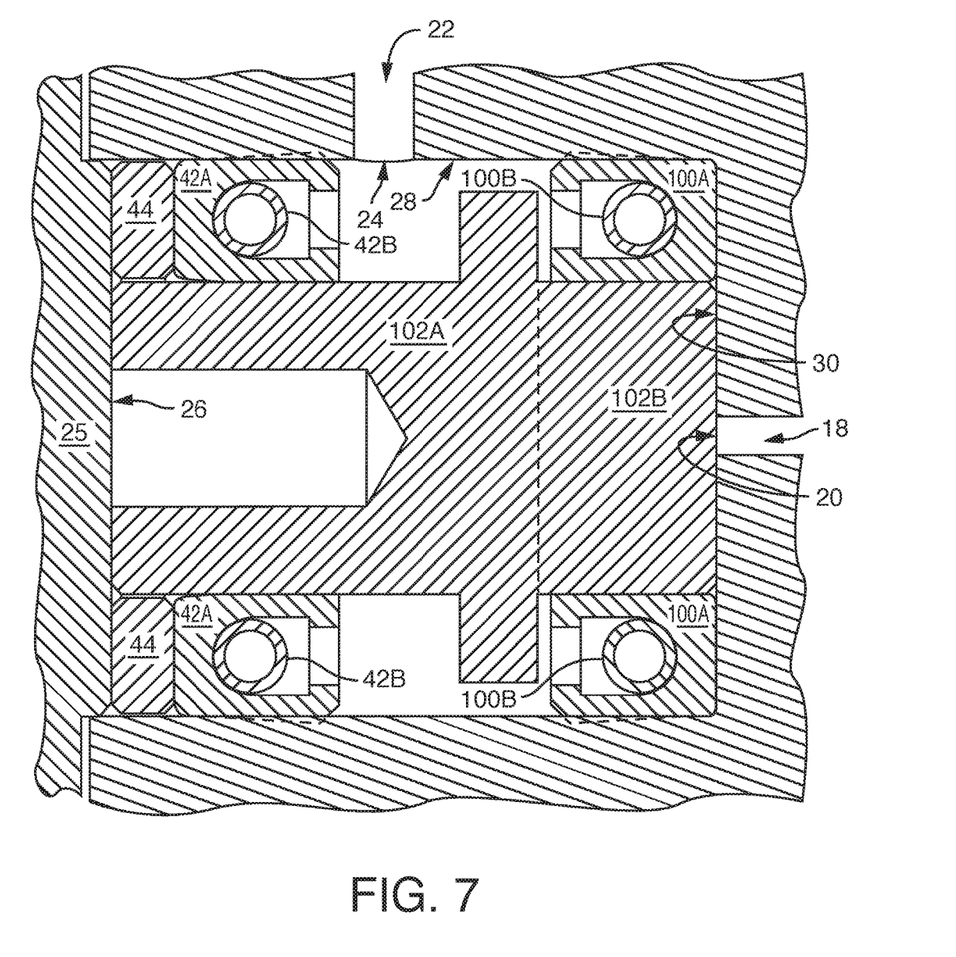
FIG. 7 is a cross-sectional view of a portion of another embodiment of a check valve.

In another alternative embodiment shown in FIG. 7, a first spring-energized seal is arranged so that its seal circumferential surface is in contact with the end surface 30 of the chamber wall. The spring 100B urges the first and second portions of the first compliant seal body 100A against the cylindrical surface 28 of the chamber wall and the cylindrical surface of the third valve body 102B. The dimensions of the second and third valve bodies 102A and 102B may be different from their counterpart bodies 14A and 14B in FIG. 1 to accommodate the difference in the orientation of the first spring-energized seals. In the illustrated embodiment, the flow of liquid from inlet channel 18 passes into the chamber through the inlet port 20 and exits the chamber through the outlet port 24 into the outlet channel 22.

Figure 8:
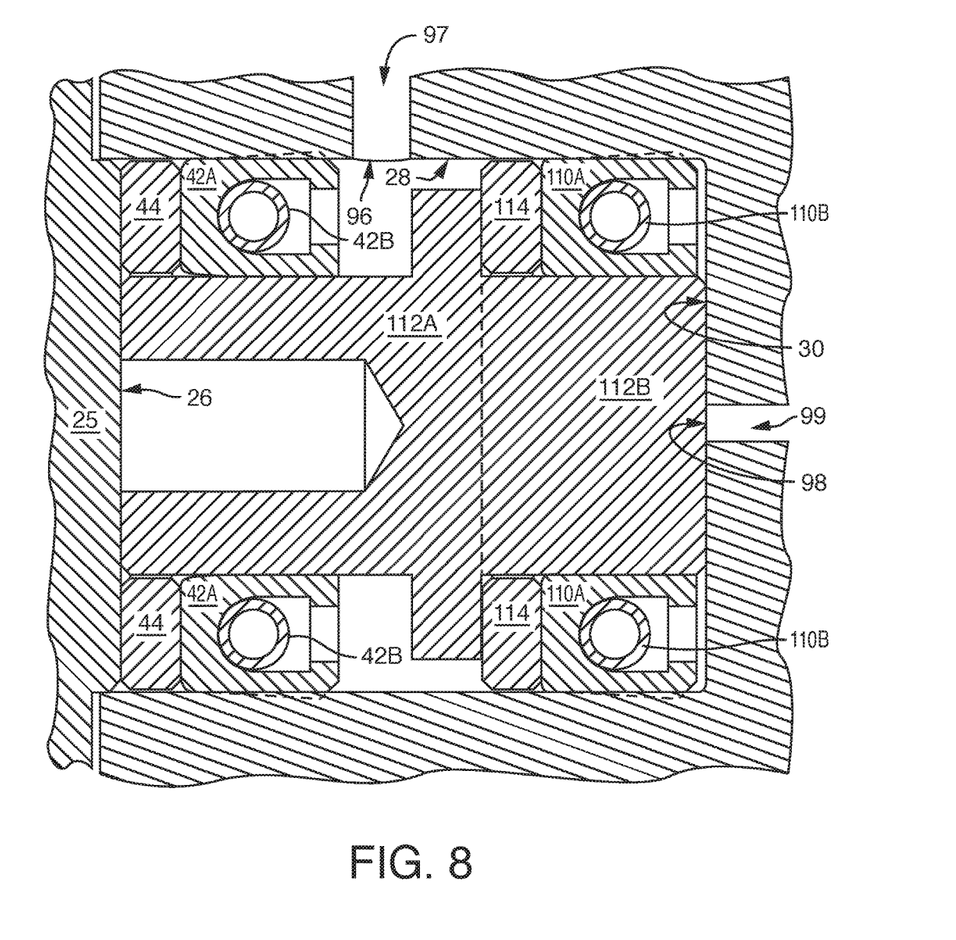
FIG. 8 is a cross-sectional view of a portion of another embodiment of a check valve.

In still another alternative embodiment shown in FIG. 8, the first spring-energized seal is configured so that the seal circumferential surface is in contact with a backing ring 114 disposed between the first compliant seal body 110A and the flange of the second valve body 112A. The spring 110B urges the first and second portions of the first compliant seal body 110A against the cylindrical surface 28 of the chamber wall and the cylindrical surface of the third valve body 112B. The dimensions of the second and third valve bodies 112A and 112B may be different from their counterpart bodies 14A and 14B in FIG. 1 to accommodate the differences in the first spring-energized seals and to accommodate the backup ring 114 used to prevent the first complaint seal body 110A from extruding to the left in the chamber. In the illustrated embodiment, liquid flows through the inlet channel 97 into the chamber through an inlet port 96 and out from the chamber through an outlet port 98 into outlet channel 99.

While the invention has been shown and described with reference to specific embodiments, it should be understood by those skilled in the art that various changes in form and detail may be made therein without departing from the scope of the invention as defined by the following claims.

What is claimed is:

1. A check valve comprising:
   a first valve body having a cylindrical chamber defined by a chamber wall comprising a cylindrical surface and an end surface, a first channel extending from a first external surface to a first port at the end surface of the chamber wall and a second channel extending from a second external surface to a second port at the cylindrical surface of the chamber wall;
   a second valve body disposed in the chamber and having a cylindrical external surface and a flange at one end;
   a third valve body having a cylindrical surface and disposed in the chamber between the flange and the end surface of the chamber wall at the inlet port; and
   a first spring-energized seal disposed in the chamber and comprising:
      a first compliant seal body having an annular shape, a seal circumferential surface and a pocket, the seal circumferential surface being in contact with the cylindrical surface of the chamber wall or the cylindrical surface of the third valve body; and
      a resilient member disposed in the pocket of the first compliant seal body, the resilient member configured to apply a force to urge a first portion of the first compliant seal body against a region of the end surface of the chamber wall surrounding the inlet port and to urge a second portion of the first compliant seal body against the flange of the second valve body.

2. The check valve of claim 1 wherein the second valve body and the third valve body are formed as a single integral body.

3. The check valve of claim 1 wherein the third valve body comprises a frit.

4. The check valve of claim 1 wherein the third valve body has a wall engagement surface at one end and adjacent to the end surface of the chamber wall, the wall engagement surface having at least one channel disposed thereon to provide a fluid path between the first port and the chamber.

5. The check valve of claim 1 further comprising a second spring-energized seal disposed in the chamber and having a second compliant seal body having a pocket with a spring disposed therein, the second compliant seal body configured to apply a force to urge a first portion of the second compliant seal body against the cylindrical surface of the chamber wall and to urge a second portion of the second compliant seal body against the cylindrical external surface of the second valve body.

6. The check valve of claim 5 wherein the first and second spring-energized seals are formed as a single integral seal assembly.

7. The check valve of claim 5 further comprising a backup ring disposed between the chamber wall and the second compliant seal body of the second spring-energized seal.

8. The check valve of claim 1 wherein the resilient member disposed in the pocket of the first compliant seal body is one of a cantered spring or an O-ring.

9. A check valve comprising:
   a first valve body having a cylindrical chamber defined by a chamber wall comprising a cylindrical surface and an end surface, a first channel extending from a first external surface to a first port at the end surface of the chamber wall and a second channel extending from a second external surface to a second port at the cylindrical surface of the chamber wall;
   a second valve body disposed in the chamber and having a cylindrical external surface and a flange at one end;
   a third valve body having a cylindrical surface and disposed in the chamber between the flange and the end surface of the chamber wall at the inlet port; and
   a first spring-energized seal disposed in the chamber and comprising:
      a first compliant seal body having an annular shape, a seal circumferential surface and a pocket, the seal circumferential surface being in contact with the end surface of the chamber wall or the flange of the second valve body; and
      a resilient member disposed in the pocket of the first compliant seal body, the resilient member configured to apply a force to urge a first portion of the first compliant seal body against the cylindrical surface of the chamber wall and to urge a second portion of the first compliant seal body against the cylindrical surface of the third valve body.

10. The check valve of claim 9 further comprising a backup ring disposed between the seal circumferential surface of the first compliant seal body and the flange of the second valve body.

11. The check valve of claim 9 wherein the second valve body and the third valve body are formed as a single integral body.

12. The check valve of claim 9 wherein the third valve body comprises a frit.

13. The check valve of claim 9 wherein the third valve body has a wall engagement surface at one end and adjacent to the end surface of the chamber wall, the wall engagement surface having at least one channel disposed thereon to provide a fluid path between the first port and the chamber.

14. The check valve of claim 9 further comprising a second spring-energized seal disposed in the chamber and having a second compliant seal body having a pocket with a spring disposed therein, the second compliant seal body configured to apply a force to urge a first portion of the second compliant seal body against the cylindrical surface of the chamber wall and to urge a second portion of the second compliant seal body against the cylindrical external surface of the second valve body.

15. The check valve of claim 14 further comprising a backup ring disposed between the chamber wall and the second compliant seal body of the second spring-energized seal.

16. The check valve of claim 14 wherein the resilient member disposed in the pocket of the first compliant seal body is one of a cantered spring or an O-ring.

* * * * *